United States Patent
Schwab et al.

(10) Patent No.: US 10,265,477 B2
(45) Date of Patent: Apr. 23, 2019

(54) MECHANICAL SYRINGE ACCESSORY

(71) Applicant: Allergan, Inc., Irvine, CA (US)

(72) Inventors: Justin J. Schwab, San Francisco, CA (US); Edwin J. Kayda, Santa Barbara, CA (US); Zachary Dominguez, Santa Barbara, CA (US); Christopher Mudd, Fort Worth, TX (US)

(73) Assignee: Allergan, Inc., Irvine, CA (US)

( * ) Notice: Subject to any disclaimer, the term of this patent is extended or adjusted under 35 U.S.C. 154(b) by 272 days.

(21) Appl. No.: 15/064,537

(22) Filed: Mar. 8, 2016

(65) Prior Publication Data

US 2016/0213854 A1 Jul. 28, 2016

Related U.S. Application Data

(62) Division of application No. 14/284,257, filed on May 21, 2014, now abandoned.
(Continued)

(51) Int. Cl.
*A61M 5/315* (2006.01)
*A61M 5/31* (2006.01)

(52) U.S. Cl.
CPC .... *A61M 5/31526* (2013.01); *A61M 5/31501* (2013.01); *A61M 5/31535* (2013.01);
(Continued)

(58) Field of Classification Search
CPC .......... A61M 5/31525; A61M 5/31526; A61M 5/31528; A61M 5/31533; A61M 5/31545; A61M 5/31548; A61M 5/3155; A61M 5/31551; A61M 5/31553; A61M 5/31565; A61M 5/31568; A61M 5/31576; A61M 5/3158; A61M 5/31581; A61M 5/31583; A61M 5/31585; A61M 5/35186; A61M 5/31591; A61M 5/31593; A61M 5/31595;
(Continued)

(56) References Cited

U.S. PATENT DOCUMENTS 2,491,978 A 12/1949 Helfman
2,737,946 A 3/1956 Hein, Jr.
(Continued)

FOREIGN PATENT DOCUMENTS

EP 362484 A2 4/1990
EP 1051988 A2 11/2000
(Continued)

OTHER PUBLICATIONS

Galderma, New Restylane Skinboosters SmartClick delivery system wins prestigious Red Dot design award, Jul. 4, 2014, http://www.galderma.com/News/articleType/ArticleView/articleId/64/New-Restylane-Skinboosters-SmartClick-delivery-system-wins-prestigious-Red-Dot-design-award.
(Continued)

*Primary Examiner* — Bhisma Mehta
*Assistant Examiner* — James D Ponton
(74) *Attorney, Agent, or Firm* — Nathan S. Smith; Andrew N. Khouzam; Morgan, Lewis & Bockius LLP

(57) ABSTRACT

Described herein are syringe accessories that can be attached to standard syringes. These accessories utilize one or more mechanisms that can provide at least one additional sensory feedback to the user when performing an aliquot or dosed injection. In other embodiments, the accessories can prevent overdosing.

18 Claims, 12 Drawing Sheets

Related U.S. Application Data

(60) Provisional application No. 61/827,221, filed on May 24, 2013, provisional application No. 61/826,827, filed on May 23, 2013.

(52) U.S. Cl.
CPC .... *A61M 5/31551* (2013.01); *A61M 5/31578* (2013.01); *A61M 5/31595* (2013.01); *A61M 2005/3126* (2013.01); *A61M 2205/581* (2013.01); *A61M 2205/582* (2013.01); *A61M 2205/583* (2013.01)

(58) Field of Classification Search
CPC .......... A61M 5/31501; A61M 5/31505; A61M 2005/31508
See application file for complete search history.

(56) References Cited

U.S. PATENT DOCUMENTS

| | | |
|---|---|---|
| 2,853,070 A | 9/1958 | Julliard |
| 3,086,530 A | 4/1963 | Groom |
| 3,161,323 A | 12/1964 | Bent |
| D202,754 S | 11/1965 | Naftolin |
| D214,112 S | 5/1969 | Langdon |
| D224,066 S | 6/1972 | McDonald |
| 3,720,211 A | 3/1973 | Kyrias |
| 3,767,085 A | 10/1973 | Cannon et al. |
| 3,807,048 A | 4/1974 | Malmin |
| 4,064,879 A | 12/1977 | Leibinsohn |
| 4,240,423 A | 12/1980 | Akhavi |
| 4,240,426 A | 12/1980 | Akhavi |
| 4,273,122 A | 6/1981 | Whitney et al. |
| 4,326,517 A | 4/1982 | Whitney et al. |
| 4,346,708 A | 8/1982 | LeVeen et al. |
| 4,444,560 A | 4/1984 | Jacklich |
| 4,529,401 A | 7/1985 | Leslie et al. |
| 4,605,691 A | 8/1986 | Balazs et al. |
| 4,624,659 A | 11/1986 | Goldberg et al. |
| 4,627,444 A | 12/1986 | Brooker |
| 4,699,612 A | 10/1987 | Hamacher |
| 4,710,172 A | 12/1987 | Jacklich et al. |
| 4,759,750 A | 7/1988 | DeVries et al. |
| 4,832,692 A * | 5/1989 | Box ................. A61M 25/1018 604/210 |
| D303,010 S | 8/1989 | Jabbusch |
| 4,869,717 A | 9/1989 | Adair |
| 4,898,572 A | 2/1990 | Surugue nee Lasnier et al. |
| 4,909,932 A | 3/1990 | Monnet |
| 5,024,613 A | 6/1991 | Vasconcellos et al. |
| 5,024,656 A | 6/1991 | Gasaway et al. |
| 5,046,506 A | 9/1991 | Singer |
| 5,100,390 A | 3/1992 | Lubeck et al. |
| 5,104,375 A | 4/1992 | Wolf et al. |
| 5,127,436 A | 7/1992 | Campion et al. |
| 5,137,181 A | 8/1992 | Keller |
| 5,141,496 A | 8/1992 | Dalto et al. |
| 5,270,685 A | 12/1993 | Hagen et al. |
| 5,279,544 A | 1/1994 | Gross et al. |
| 5,295,980 A | 3/1994 | Ersek |
| 5,305,788 A | 4/1994 | Mayeux |
| 5,318,544 A * | 6/1994 | Drypen ............... A61M 5/3155 604/210 |
| 5,322,511 A | 6/1994 | Armbruster et al. |
| 5,344,407 A | 9/1994 | Ryan |
| 5,368,572 A | 11/1994 | Shirota |
| 5,383,851 A | 1/1995 | McKinnon, Jr. et al. |
| 5,405,330 A | 4/1995 | Zunitch et al. |
| 5,520,658 A | 5/1996 | Holm |
| 5,540,657 A | 7/1996 | Kurjan et al. |
| 5,584,815 A | 12/1996 | Pawelka et al. |
| D378,939 S | 4/1997 | Smith et al. |
| 5,650,317 A | 7/1997 | Chang et al. |
| 5,690,618 A | 11/1997 | Smith et al. |
| 5,716,404 A | 2/1998 | Vacanti et al. |
| 5,722,829 A | 3/1998 | Wilcox et al. |
| 5,728,077 A | 3/1998 | Williams et al. |
| 5,807,340 A | 9/1998 | Pokras |
| 5,814,511 A | 9/1998 | Chang et al. |
| 5,817,033 A | 10/1998 | DeSantis et al. |
| 5,853,388 A | 12/1998 | Semel |
| 5,972,385 A | 10/1999 | Liu et al. |
| 6,047,861 A | 4/2000 | Vidal et al. |
| D424,194 S | 5/2000 | Holdaway et al. |
| 6,082,364 A | 7/2000 | Balian et al. |
| 6,083,912 A | 7/2000 | Khouri |
| 6,129,761 A | 10/2000 | Hubbell |
| 6,171,610 B1 | 1/2001 | Vacanti et al. |
| 6,176,396 B1 | 1/2001 | Hamada et al. |
| 6,183,434 B1 | 2/2001 | Eppstein |
| D441,077 S | 4/2001 | Garito et al. |
| 6,214,045 B1 | 4/2001 | Corbitt, Jr. et al. |
| 6,231,552 B1 | 5/2001 | Jentzen |
| 6,239,105 B1 | 5/2001 | Brewitt |
| 6,312,412 B1 | 11/2001 | Saied et al. |
| 6,316,247 B1 | 11/2001 | Katz et al. |
| 6,432,046 B1 | 8/2002 | Yarush et al. |
| 6,582,960 B1 | 6/2003 | Martin et al. |
| 6,607,512 B2 | 8/2003 | Oliver et al. |
| 6,610,033 B1 | 8/2003 | Melanson et al. |
| 6,613,010 B2 | 9/2003 | Castellano |
| 6,616,448 B2 | 9/2003 | Friedman |
| 6,638,308 B2 | 10/2003 | Corbitt, Jr. et al. |
| D483,116 S | 12/2003 | Castellano |
| 6,656,488 B2 | 12/2003 | Yi et al. |
| 6,666,893 B2 | 12/2003 | Burg et al. |
| 6,689,095 B1 | 2/2004 | Garitano et al. |
| 6,689,103 B1 | 2/2004 | Palasis |
| 6,777,231 B1 | 8/2004 | Katz et al. |
| 6,780,171 B2 | 8/2004 | Gabel et al. |
| 6,783,514 B2 | 8/2004 | Tovey et al. |
| 6,824,526 B2 | 11/2004 | Castellano |
| 6,881,226 B2 | 4/2005 | Corbitt, Jr. et al. |
| 6,896,666 B2 | 5/2005 | Kochamba |
| 6,908,453 B2 | 6/2005 | Fleming et al. |
| 6,916,603 B2 | 7/2005 | Baron et al. |
| 6,945,952 B2 | 9/2005 | Kwon |
| 6,991,652 B2 | 1/2006 | Burg |
| 7,004,928 B2 | 2/2006 | Aceti et al. |
| 7,015,037 B1 | 3/2006 | Furcht et al. |
| 7,018,356 B2 | 3/2006 | Wise et al. |
| 7,047,070 B2 | 5/2006 | Wilkinson et al. |
| 7,097,631 B2 | 8/2006 | Trautman et al. |
| 7,108,681 B2 | 9/2006 | Gartstein et al. |
| 7,129,209 B2 | 10/2006 | Rhee |
| 7,285,266 B2 | 10/2007 | Vournakis et al. |
| 7,316,822 B2 | 1/2008 | Binette et al. |
| 7,390,484 B2 | 6/2008 | Fraser et al. |
| 7,419,472 B2 | 9/2008 | Hibner et al. |
| 7,445,793 B2 | 11/2008 | Niwa et al. |
| 7,494,473 B2 | 2/2009 | Eggers et al. |
| 7,501,115 B2 | 3/2009 | Fraser et al. |
| 7,514,075 B2 | 4/2009 | Hedrick et al. |
| 7,556,615 B2 | 7/2009 | Pettis et al. |
| 7,560,276 B2 | 7/2009 | Harmon et al. |
| 7,588,547 B2 | 9/2009 | Deem et al. |
| 7,611,495 B1 | 11/2009 | Gianturco |
| 7,651,475 B2 | 1/2010 | Angel et al. |
| 7,651,684 B2 | 1/2010 | Hedrick et al. |
| D615,192 S | 5/2010 | Mudd et al. |
| 7,767,452 B2 | 8/2010 | Kleinsek |
| 7,799,767 B2 | 9/2010 | Lamberti et al. |
| 7,850,683 B2 | 12/2010 | Elkins et al. |
| 7,875,296 B2 | 1/2011 | Binette et al. |
| 7,878,981 B2 | 2/2011 | Strother et al. |
| 7,896,837 B2 | 3/2011 | Wilkinson et al. |
| D637,287 S | 5/2011 | Mudd et al. |
| 8,029,460 B2 | 10/2011 | Rush et al. |
| 8,053,423 B2 | 11/2011 | Lamberti et al. |
| 8,066,629 B2 | 11/2011 | Dlugos |
| 8,066,691 B2 | 11/2011 | Khouri |
| 8,137,705 B2 | 3/2012 | Doyle et al. |
| 8,153,591 B2 | 4/2012 | Masters et al. |
| 8,157,830 B2 | 4/2012 | Wenchell |

(56) References Cited

U.S. PATENT DOCUMENTS

| | | |
|---|---|---|
| 8,216,190 B2 | 7/2012 | Gartstein et al. |
| 8,236,021 B2 | 8/2012 | Kluge et al. |
| 8,291,768 B2 | 10/2012 | Spiegel et al. |
| 8,303,518 B2 | 11/2012 | Aceti et al. |
| 8,343,132 B2 | 1/2013 | Heneveld et al. |
| 8,349,554 B2 | 1/2013 | Bahrami et al. |
| 8,353,871 B2 | 1/2013 | Zimmerman et al. |
| 8,366,643 B2 | 2/2013 | Deem et al. |
| 8,409,185 B2 | 4/2013 | Burger et al. |
| 8,480,630 B2 | 7/2013 | Mudd et al. |
| 8,603,028 B2 | 12/2013 | Mudd et al. |
| 8,657,786 B2 | 2/2014 | Bahrami et al. |
| 8,668,675 B2 | 3/2014 | Chase et al. |
| 8,821,446 B2 | 9/2014 | Trautman et al. |
| 8,900,181 B2 | 12/2014 | Knowlton |
| 8,900,186 B2 | 12/2014 | Pettis et al. |
| 9,017,289 B2 | 4/2015 | Backes |
| 9,017,318 B2 | 4/2015 | Fourkas et al. |
| 9,039,688 B2 | 5/2015 | Palmer, III et al. |
| 9,066,712 B2 | 6/2015 | Fourkas et al. |
| 9,072,498 B2 | 7/2015 | Elkins et al. |
| 9,101,346 B2 | 8/2015 | Burger et al. |
| 9,113,855 B2 | 8/2015 | Burger et al. |
| 9,149,331 B2 | 10/2015 | Deem et al. |
| 9,155,584 B2 | 10/2015 | Fourkas et al. |
| 9,241,753 B2 | 1/2016 | Fourkas et al. |
| 9,254,162 B2 | 2/2016 | Burger et al. |
| 2002/0010433 A1 | 1/2002 | Johnson et al. |
| 2002/0065483 A1 | 5/2002 | Leon et al. |
| 2002/0151843 A1 | 10/2002 | Correa et al. |
| 2003/0050602 A1 | 3/2003 | Pettis et al. |
| 2003/0078912 A1 | 4/2003 | Oliver et al. |
| 2003/0144632 A1 | 7/2003 | Hommann et al. |
| 2003/0181863 A1 | 9/2003 | Ackley et al. |
| 2003/0199883 A1 | 10/2003 | Laks |
| 2003/0233067 A1 | 12/2003 | McIntosh et al. |
| 2004/0092011 A1 | 5/2004 | Wilkison et al. |
| 2004/0092927 A1 | 5/2004 | Podhajsky et al. |
| 2004/0147883 A1 | 7/2004 | Tsai |
| 2005/0025755 A1 | 2/2005 | Hedrick et al. |
| 2005/0085767 A1 | 4/2005 | Menassa |
| 2005/0123895 A1 | 6/2005 | Freund |
| 2005/0131353 A1 | 6/2005 | Mossanen-Shams et al. |
| 2005/0137496 A1 | 6/2005 | Walsh et al. |
| 2005/0147562 A1 | 7/2005 | Hunter et al. |
| 2005/0215956 A1 | 9/2005 | Nerney |
| 2005/0261633 A1 | 11/2005 | Khalaj |
| 2006/0079765 A1 | 4/2006 | Neer et al. |
| 2006/0089594 A1 | 4/2006 | Landau |
| 2006/0150742 A1 | 7/2006 | Esnouf |
| 2007/0038181 A1 | 2/2007 | Melamud et al. |
| 2007/0083155 A1 | 4/2007 | Muller |
| 2007/0100363 A1 | 5/2007 | Dollar et al. |
| 2007/0191781 A1 | 8/2007 | Richards et al. |
| 2007/0212385 A1 | 9/2007 | David |
| 2007/0250010 A1 | 10/2007 | Hohlfelder et al. |
| 2007/0251531 A1 | 11/2007 | Khouri |
| 2008/0015522 A1 | 1/2008 | Yeshurun et al. |
| 2008/0033347 A1 | 2/2008 | D'Arrigo et al. |
| 2008/0058706 A1 | 3/2008 | Zhang et al. |
| 2008/0071385 A1 | 3/2008 | Binette et al. |
| 2008/0097325 A1 | 4/2008 | Tanaka et al. |
| 2008/0108952 A1 | 5/2008 | Horvath et al. |
| 2008/0114305 A1 | 5/2008 | Gerondale |
| 2008/0188816 A1 | 8/2008 | Shimazaki et al. |
| 2008/0200758 A1 | 8/2008 | Orbay et al. |
| 2008/0243028 A1 | 10/2008 | Howard et al. |
| 2008/0281278 A1 | 11/2008 | Williams, Jr. et al. |
| 2008/0299213 A2 | 12/2008 | Kleinsek et al. |
| 2008/0317718 A1 | 12/2008 | Yoshimura |
| 2009/0088703 A1 | 4/2009 | Azar |
| 2009/0098177 A1 | 4/2009 | Werkmeister et al. |
| 2009/0123547 A1 | 5/2009 | Hill et al. |
| 2009/0124552 A1 | 5/2009 | Hill et al. |
| 2009/0124996 A1 | 5/2009 | Heneveld et al. |
| 2009/0125050 A1 | 5/2009 | Dixon |
| 2009/0131886 A1 | 5/2009 | Liu et al. |
| 2009/0143746 A1 | 6/2009 | Mudd et al. |
| 2009/0162415 A1 | 6/2009 | Huang et al. |
| 2009/0240200 A1 | 9/2009 | Heneveld et al. |
| 2009/0246182 A1 | 10/2009 | Casteilla et al. |
| 2009/0247953 A1 | 10/2009 | Yeshurun et al. |
| 2009/0287161 A1 | 11/2009 | Traub et al. |
| 2009/0299328 A1 | 12/2009 | Mudd et al. |
| 2009/0312746 A1 | 12/2009 | Khouri |
| 2009/0317367 A1 | 12/2009 | Chazenbalk et al. |
| 2010/0010627 A1 | 1/2010 | Matheny |
| 2010/0069848 A1 | 3/2010 | Alferness et al. |
| 2010/0121307 A1 | 5/2010 | Lockard et al. |
| 2010/0152675 A1 | 6/2010 | McClintock |
| 2010/0152679 A1 | 6/2010 | Tezel et al. |
| 2010/0179488 A1 | 7/2010 | Spiegel et al. |
| 2010/0256594 A1 | 10/2010 | Kimmell et al. |
| 2010/0279405 A1 | 11/2010 | Peterson et al. |
| 2010/0280488 A1 | 11/2010 | Pruitt et al. |
| 2010/0282774 A1 | 11/2010 | Greter et al. |
| 2011/0021905 A1 | 1/2011 | Patrick et al. |
| 2011/0028910 A1 | 2/2011 | Weber |
| 2011/0070281 A1 | 3/2011 | Altman et al. |
| 2011/0092916 A1 | 4/2011 | Tezel et al. |
| 2011/0137286 A1 | 6/2011 | Mudd et al. |
| 2011/0150823 A1 | 6/2011 | Huang |
| 2011/0160674 A1 | 6/2011 | Holmes et al. |
| 2011/0172645 A1 | 7/2011 | Moga et al. |
| 2011/0202014 A1 | 8/2011 | Mutzbauer |
| 2011/0213336 A1 | 9/2011 | Cucin |
| 2011/0218497 A1 | 9/2011 | Assaf |
| 2011/0230839 A1 | 9/2011 | Bahrami et al. |
| 2011/0238038 A1 | 9/2011 | Sefi et al. |
| 2011/0282324 A1 | 11/2011 | Kurokawa et al. |
| 2011/0282381 A1 | 11/2011 | Cronin et al. |
| 2011/0319865 A1 | 12/2011 | Buss |
| 2012/0010146 A1 | 1/2012 | Han et al. |
| 2012/0076868 A1 | 3/2012 | Lamberti et al. |
| 2012/0089211 A1 | 4/2012 | Curtis et al. |
| 2012/0101475 A1 | 4/2012 | Wilmot et al. |
| 2012/0123194 A1 | 5/2012 | Beckman et al. |
| 2012/0150266 A1 | 6/2012 | Shalev et al. |
| 2012/0156265 A1 | 6/2012 | Binette et al. |
| 2012/0209248 A1 | 8/2012 | Gurtner et al. |
| 2012/0259322 A1 | 10/2012 | Fourkas et al. |
| 2012/0265064 A1 | 10/2012 | Bahrami et al. |
| 2012/0265171 A1 | 10/2012 | Thorne, Jr. et al. |
| 2012/0296206 A1 | 11/2012 | Bahrami et al. |
| 2013/0041346 A1 | 2/2013 | Alon |
| 2013/0131632 A1 | 5/2013 | Mudd et al. |
| 2013/0131633 A1 | 5/2013 | Mudd et al. |
| 2013/0150826 A1 | 6/2013 | Almohizea |
| 2013/0184696 A1 | 7/2013 | Fourkas et al. |
| 2013/0197446 A1* | 8/2013 | Gustafsson ....... A61M 5/31595 604/189 |
| 2013/0197449 A1* | 8/2013 | Franklin ........... A61M 5/31526 604/209 |
| 2013/0253289 A1 | 9/2013 | Hadvary et al. |
| 2013/0274655 A1 | 10/2013 | Jennings et al. |
| 2013/0274670 A1 | 10/2013 | Mudd et al. |
| 2013/0280755 A1 | 10/2013 | Hubert |
| 2014/0018770 A1 | 1/2014 | Sutkin |
| 2014/0018835 A1 | 1/2014 | Scherkowski et al. |
| 2014/0066845 A1 | 3/2014 | Mudd et al. |
| 2014/0088502 A1 | 3/2014 | Matheny et al. |
| 2014/0088553 A1 | 3/2014 | Hetherington |
| 2014/0114279 A1 | 4/2014 | Klinghoffer |
| 2014/0128685 A1 | 5/2014 | Na |
| 2014/0170299 A1 | 6/2014 | Gill et al. |
| 2014/0257179 A1 | 9/2014 | Schwab et al. |
| 2014/0350514 A1 | 11/2014 | Levin |
| 2014/0350516 A1 | 11/2014 | Schwab et al. |
| 2014/0350517 A1 | 11/2014 | Dominguez et al. |
| 2014/0350518 A1 | 11/2014 | Franklin et al. |
| 2014/0350536 A1 | 11/2014 | Allison |
| 2015/0126929 A1 | 5/2015 | Franklin et al. |
| 2015/0343147 A1 | 12/2015 | Franklin et al. |

(56) References Cited

U.S. PATENT DOCUMENTS

| | | |
|---|---|---|
| 2016/0058488 A1 | 3/2016 | Fourkas et al. |
| 2016/0095984 A1 | 4/2016 | Franklin et al. |
| 2016/0144125 A1 | 5/2016 | Franklin et al. |

FOREIGN PATENT DOCUMENTS

| | | |
|---|---|---|
| EP | 1486218 A2 | 12/2004 |
| EP | 1859827 A1 | 11/2007 |
| EP | 1923086 A1 | 5/2008 |
| EP | 1476202 B1 | 1/2009 |
| EP | 2189173 A2 | 5/2010 |
| EP | 2335755 A1 | 6/2011 |
| FR | 2622457 A1 | 5/1989 |
| WO | 1994012228 A1 | 6/1994 |
| WO | 1999048601 A1 | 9/1999 |
| WO | 2002055135 A2 | 7/2002 |
| WO | 2005095225 A1 | 10/2005 |
| WO | 20060133111 A2 | 12/2006 |
| WO | WO-2007/095922 A1 | 8/2007 |
| WO | WO-2007/124478 A2 | 11/2007 |
| WO | 2008019265 A2 | 2/2008 |
| WO | 2008053481 A1 | 5/2008 |
| WO | WO-2008/063569 A1 | 5/2008 |
| WO | 2008072229 A2 | 6/2008 |
| WO | 2008079824 A2 | 7/2008 |
| WO | WO-2008/148026 A1 | 12/2008 |
| WO | WO-2008/148071 A2 | 12/2008 |
| WO | WO-2009/003135 A1 | 12/2008 |
| WO | WO-2009/047346 A1 | 4/2009 |
| WO | WO-2009/085548 A2 | 7/2009 |
| WO | 2009098666 A1 | 8/2009 |
| WO | WO-2009/103818 A1 | 8/2009 |
| WO | WO-2009/115581 A2 | 9/2009 |
| WO | 2009158145 A2 | 12/2009 |
| WO | WO-2009/155583 A1 | 12/2009 |
| WO | WO-2010/026299 A1 | 3/2010 |
| WO | WO-2010/127310 A1 | 11/2010 |
| WO | WO-2011/072399 A1 | 6/2011 |
| WO | WO-2012/006587 A2 | 1/2012 |
| WO | WO-2012/019103 A2 | 2/2012 |
| WO | 2013005881 A1 | 1/2013 |
| WO | WO-2013/054165 A1 | 4/2013 |
| WO | 2013106857 A1 | 8/2013 |
| WO | 2014026044 A2 | 2/2014 |
| WO | 2015020982 A2 | 2/2015 |
| WO | 2015149031 A1 | 10/2015 |
| WO | 2016022865 A1 | 2/2016 |
| WO | 2016033584 A1 | 3/2016 |
| WO | 2016033586 A1 | 3/2016 |

OTHER PUBLICATIONS

Prime Journal, Galderma to launch two new syringes at AMWC 2014, Mar. 20, 2014.

Turtlepin, The Painless Direct Dermal Injector—Product Information, JM Biotech Co., Ltd., 2013.

Davidenko et al., "Collagen-hyaluronic acid scaffolds for adipose tissue engineering", ACTA Biomaterialia, vol. 6, No. 10, Oct. 1, 2010, pp. 3957-3968, XP055055114.

Kilroy, Gail et al., Cytokine Profile of Human Adipose-Derived Stem Cells: Expression of Angiogenic, Hematopoietic, and Pro-Inflammatory Factors, J. Cell. Physiol., 2007, 702-709, 212.

Park et al., "Biological characterization of EDC-crosslinked collagen-hyaluronic acid matrix in dermal tissue restoration", Biomaterials, Elsevier Science Publishers BV, vol. 24, No. 9, Apr. 1, 2003, pp. 1631-1641, XP004404219.

Rehman, Jalees et al., Secretion of Angiogenic and Antiapoptotic Factors by Human Adipose Stromal Cells, Circulation, 2004, 1292-1298, 109.

Wang et al., "In vivo stimulation of de novo collagen production caused by cross-linked hyaluronic acid dermall filler injections in photodamaged human skin.", Archives of Dermatology, American Medical Association, US, vol. 143, No. 2, Feb. 1, 2007, pp. 155-163, XP002574140.

Yoshimura, Kotaro et al., Cell-Assisted Lipotransfer for Cosmetic Breast Augmentation: Supportive Use of Adipose-Derived Stem/Stromal Cells, Aesth. Plast. Surg., 2008, 48-55, 32.

Yoshimura, Kotaro et al., Cell-Assisted Lipotransfer for Facial Lipoatrophy: Effects of Clinical Use of Adipose-Derived Stem Cells, Dermatol. Surg., 2008, 1178-1185, 34.

Yoshimura, Kotaro et al., Characterization of Freshly Isolated and Cultured Cells Derived From the Fatty and Fluid Portions of Liposuction Aspirates, J Cell Physiol, 2006, 1011-1041, 208.

International Search Report and Written Opinion from PCT/US2014/039265, dated Nov. 18, 2014, 17 pages.

International Search Report and Written Opinion from PCT/US2014/039266, dated Aug. 26, 2014, 13 pages.

* cited by examiner

Methods of measuring aliquot/dose syringe injections

| Visible (light feedback) | Tactile (force feedback) | Audible (sound feedback) |

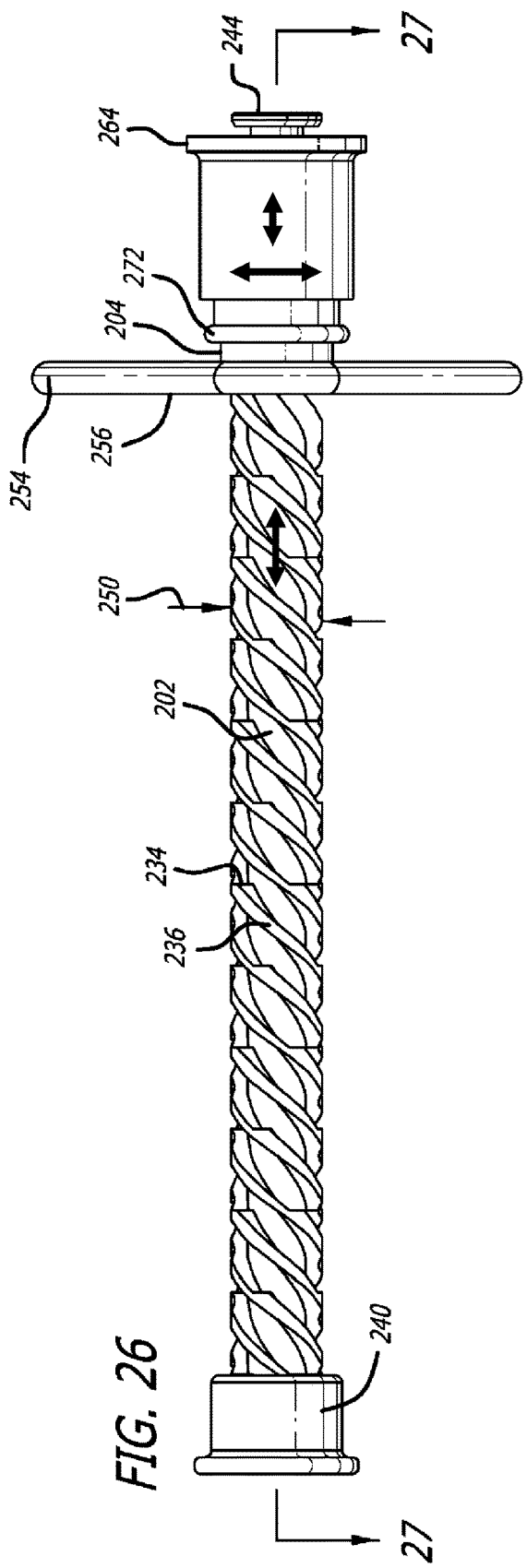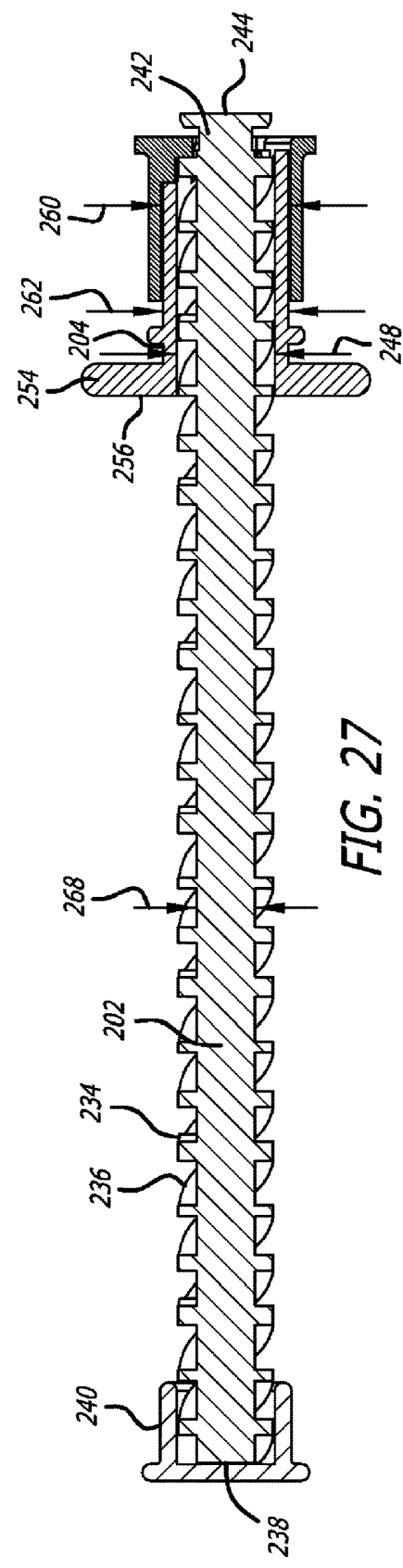

MECHANICAL SYRINGE ACCESSORY

CROSS REFERENCE TO RELATED APPLICATIONS

This application is a Divisional of U.S. patent application Ser. No. 14/284,257, filed on May 21, 2014, which claims the benefit of U.S. provisional patent application No. 61/826,827, filed May 23, 2013 and U.S. provisional patent application No. 61/827,221, filed May 24, 2013, the entire disclosure of each of these documents being incorporated herein by this specific reference.

FIELD

The present invention generally relates to medical injection device accessories, and more specifically relates to a medical syringe accessory designed to facilitate aliquot dosing.

BACKGROUND

The ability to accurately assess correct injection dosage is most commonly associated with visual cues. For example, volumetric marks already come printed or etched on the side of conventional syringe bodies, and this remains the most common form of measurement. A practitioner injects a certain amount of a substance, such as a drug, by verifying fluid level using these volumetric marks.

Even more generally, a physician can intake an amount of a drug to be injected into the syringe using the volumetric marks. Then, a practitioner can simply expel the entire volume into a patient in a single plunger run. Such a full expulsion of drug removed the need to only inject a portion of a drug in a syringe. Thus, for pharmaceutical drugs, the benefits of injecting the correct dosage should not require explanation.

However, in applications using sensitive drugs such as botulinum toxin or aesthetic soft tissue fillers, for example, hyaluronic acid-based dermal fillers such as Juvederm® XC, manufactured by Allergan, Inc., dose indication provides the practitioner with additional control over precise facial sculpting.

Additionally, with applications like botulinum toxin injection, of multiple small, precise doses of toxin may be advantageous over injection of a large bolus of the material.

Further, with fat grafting, injection of multiple small, precise doses of fat cell-containing material may be advantageous over injection of a single large bolus of the material. Smaller bolus injection increases retention of the injected material, possibly by providing greater vascularization of the material throughout the fat cells and improving survivability thereof. Injection of a large bolus is less likely to be retained long term as the injected fat cells be may be more prone to die, due to lack of vascularization, for example.

Many of these injectable materials, for example, dermal fillers and fat grafting materials, are not easily extruded through standard syringes and accompanying cannula. These materials tend to provide significant resistance to be pushed through a narrow cannula. The problem is even more exacerbated by the fact that these materials are often used for detailed precision work in facial contouring and body sculpting.

Injection devices, both manual and motorized, have been specifically developed, or at least proposed, to address these issues. Interestingly, many physicians prefer the use of manual conventional syringe injectors over electronically controlled, motorized devices. For at least this reason, there remains a need for devices (e.g., simple devices) that can be attached to a standard syringe and which provide better control over small aliquot dosing of relatively difficult to inject materials, for example, dermal fillers, fat grafting materials and the like.

SUMMARY

Disclosed herein are dosing accessories configured to be attached or coupled to standard syringes. The dosing accessories are configured to provide improved mechanical advantage and aliquot dosing capability, relative to a conventional syringe alone. In some embodiments, the accessories described can be used in conjunction with conventional syringes for injection of the dermal fillers or fat grafting materials.

In one embodiment, accessories for a syringe are described comprising: a finger portion configured to attach to the body of the syringe wherein the finger portion includes a track guide including a lever arm; a track configured to insert through the track guide and including valleys separated by a distance; and a plunger interface configured to attach the track to a plunger of the syringe. The distance between adjacent valleys can correspond to a pre-determined dose of a substance housed in the syringe.

In some embodiments, the finger portion may be configured to attach to a flange of the syringe. In some embodiments, the valleys may be located on a top surface of the track and/or the lever can be configured to lock in the valleys.

In other embodiments, the valleys may be formed between peaks having a long front surface and a short back surface and the lever arm can be configured to lock against the short back surface. In other embodiments, a peak exists between each valley and the peak can have a rounded shape rendering the accessory reusable.

In still other embodiments, the valleys may be located on a bottom surface of the track. Therein, the lever arm can be configured to apply a force on a top surface of the tracks and cause a protrusion to engage with the valleys.

In one embodiment, accessories for a syringe are described comprising: a shaft including features that are configured to define at least one dose increment and having a horizontal degree of freedom, a rotating traveler including a horizontal degree of freedom and a vertical degree of freedom; and a fixed ratchet including valleys configured to engage the rotating traveler. The fixed ratchet may not interact with the rotating traveler. Also, the shaft may be at least partially attached to the plunger.

In some embodiments, the fixed ratchet may be attached to a flange on the syringe.

Further, the shaft can be configured to move with the horizontal degree of freedom to engage the rotating traveler. Also, the rotating traveler can include a spring that provides the horizontal degree of freedom.

In other embodiments, when a first dose increment is reached, the accessory can be reset for a subsequent dose increment.

Some embodiments provide a shaft comprising at least one spiral including intermittent stops. The rotating traveler can spin around the at least one spiral on the shaft.

Methods of injecting an aliquot dose of a substance using a standard syringe and an accessory as described herein are also described. In one embodiment, the method comprises: attaching an accessory including a track guide to a body portion of the syringe such as a finger flange; inserting a track into the track guide until a portion of the track engages with a plunger head associated with the syringe; and applying a force to the plunger head thereby advancing the tracks through the track guide; wherein the advancing causes at least one audible cue that represents an aliquot dose.

In some embodiments, the at least one audible cue can be a lever arm associated with the track guide snapping over a peak in the track.

Further, applying a force to the plunger head advances a plunger tip and extrudes the substance from the standard syringe.

In another example embodiment, methods comprise: applying an injection force to a shaft including at least one spiral including at least one intermittent distance between at least one first stop and at least one second stop, wherein the injection force drives the shaft axially through a rotating traveler the intermittent distance, and wherein the intermittent distance represents an aliquot dose.

In some embodiments, the rotating traveler can lock when it engages the second stop. Then, a release of force on the shaft can unlock the rotating traveler and allow a subsequent aliquot dose.

The accessories described herein can be single use, disposable devices or can be configured to be reusable with multiple types of standard syringes.

BRIEF DESCRIPTION OF THE DRAWINGS

Embodiments of the present description are illustrated by way of example, and not by way of limitation, in the figures of the accompanying drawings and in which like reference numerals refer to similar elements, wherein:

FIG. 26 is a side view of the assembled components illustrated in FIG. 25.

FIG. 27 is a cross-sectional view as outlined in FIG. 26.

DETAILED DESCRIPTION

Generally described herein are syringe accessories that can be attached to a conventional syringe. General syringes provide visual feedback in the form of visible indicia, for example, volumetric marks, provided on the syringe barrel. The accessories described herein can provide one or more mechanisms that can provide at least one additional sensory feedback to the user when performing an aliquot or dosed injection. These one or more additional sensory feedbacks can be audible or tactile in addition to being visual. In some embodiments, no visual feedback is required.

Aliquot or dosed injection generally relies upon the user observing the advancement of a plunger head in the transparent syringe barrel. The practitioner can utilize visible indicia, for example, volumetric marks, provided on the syringe barrel to determine the amount of substance injected.

The accessories described herein can enhance or replace this use of visible indicia with one or more additional sensory feedbacks to assist in determining dosage during injection. These sensory feedbacks are illustrated, for example, in FIG. 1.

In one embodiment, a tactile or force feedback mechanism can assist in aliquot dosing by providing a user with a sensation when a particular amount of substance has been injected.

In another embodiment, an audible or sound feedback mechanism can assist in aliquot dosing by providing a user with an audible cue when a particular amount of substance has been injected. In some embodiments, this audible cue can be a snap or click.

Figures 1, 2:
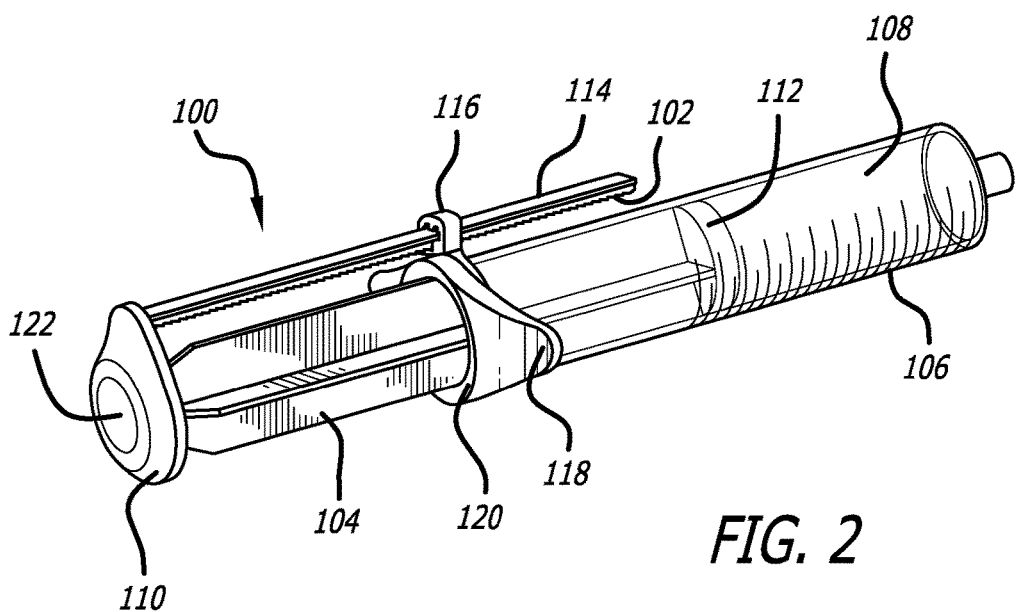
FIG. 1 illustrates three feedbacks that can be provided during an injection procedure.
FIG. 2 illustrates a perspective view of an example accessory as described herein attached to a standard syringe.

In one embodiment, shown generally in FIG. 2, accessory device 100 includes a plurality of ratchets 102. Each ratchet can represent a specific amount of travel by plunger 104. Discrete amounts of plunger travel can translate to discrete aliquot or dosed injection. In other embodiments, amounts of plunger travel do not translate to a discrete aliquot or dosed injection, but rather require a user to gauge a dose based on visual markings 106 on syringe body 108.

Accessory device 100 further includes a plunger cover 110 that physically covers or engages the plunger head (not illustrated). Plunger cover 110 allows force applied to it to be directly applied to the plunger head thereby moving piston 112 through syringe body 108.

Plunger cover 110 can have virtually any shape that allows finger force to be applied and translated into axial force on piston 112. For example, plunger cover 110 can be circular, square, pentagonal, hexagonal, heptagonal, octagonal, or any other rectilinear shape.

Ratchets 102 are included on a track 114 that is guided axially along syringe body 108 by track guide 116. Track guide 116 is attached to flange portion 118. Flange portion 118 can circumferentially surround syringe flange 120 and be configured to be the key attachment point for accessory 100. Flange portion 118 can be shaped to at least partially engage syringe flange 120. In some embodiments, flange portion 118 can engage between about 20% and about 80%, between about 30% and about 60%, between about 40% and about 60%, between about 50% and about 70%, or between about 60% and about 80% of syringe flange 120. Flange portion 118 can engage with syringe flange 120 using a friction fit, a locking fit where flange portion 118 includes locking features that snap and lock once the two parts are engaged, or a glue engagement wherein flange portion 118 and syringe flange 120 are glued together. In some embodiments, accessory 100 can be permanently attached to a syringe.

Once a finger, such as a thumb, is depressed against plunger cover 110 such as in finger depression 122, force can be translated into movement of plunger 104 and piston 112.

Figure 3:
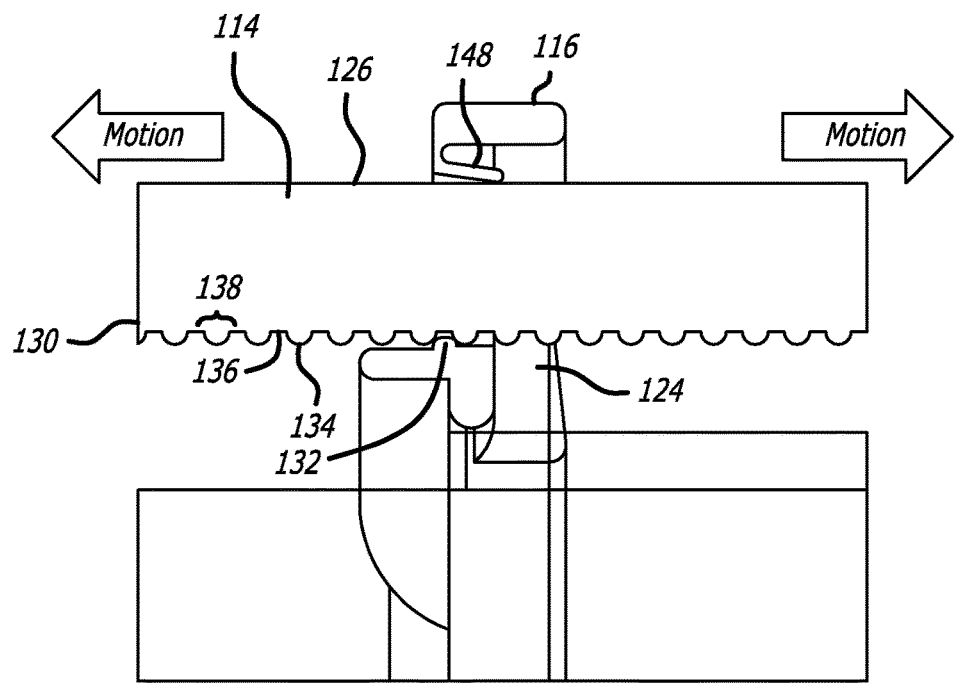
FIG. 3 illustrates a sectional view of a track engaged with a track guide.

An exemplary track system is illustrated in FIGS. 2-3. Track system includes track 114 traveling through track guide 116. Track guide 116 can include a track orifice 124 with a shape complimentary to the cross section of track 114. Downward force is applied to top side 126 of track 114 by lever arm 148. Lever arm 148 can be bent in an upward direction thereby spacing bottom side 130 of track 114 from protrusion 132 thereby allowing track 114 to progress axially.

Protrusion 132 can be configured to engage tracks 114 between adjacent ratcheting teeth 134. In some embodiments, ratcheting teeth 134 can have a generally rounded or oval surface preventing glove tears and allowing for bi-directional motion. Bi-directional motion can allow reusability of the accessory.

Each valley 136 between adjacent ratcheting teeth 134 can be spaced 138 from the next valley. Each spacing 138 can be equivalent to a predetermined amount of substance ejected from the syringe. This is the case because movement of track 114 a particular distance moves plunger cover 110 which eventually moves piston 112 the same axial distance.

Another exemplary track system is illustrated in FIGS. 4-17. Track system includes track 140 traveling through track guide 142. Track guide 142 can include a track orifice 144 with a shape complimentary to the cross section of track 140. Ratcheting teeth 146 can be located on top side 126 of track 140. Lever arm 148 can be bent in an upward direction thereby moving it from one valley(s) 150 to the next between ratcheting teeth 146. Lever arm 148 may be the primary ratchet mechanism, applying downward force on ratcheting teeth 146.

Ratcheting teeth 146 can have a wave shape with a long front surface 152 and a short back surface 154. As track 140 is moved to the right, lever arm 148 can be bent upward along long front surface 152 until the peak is reached and it snaps into an adjacent valley 150. Once in a valley 150, the angle of short back surface 154 prevents track 140 from moving left because lever arm 148 locks track 140 in place. Track 140 rests against flange portion 118 preventing it from moving downward and allowing unlocking of track 140.

Each valley 150 between adjacent ratcheting teeth 146 can be spaced 156 from the next valley. Each spacing 156 can be equivalent to a predetermined amount of substance ejected from the syringe. This is the case because movement of track 140 a particular distance moves plunger cover 110 which eventually moves piston 112 the same axial distance.

In some embodiments, the track system illustrated in FIGS. 4-17 represents a single use design.

Figure 5:
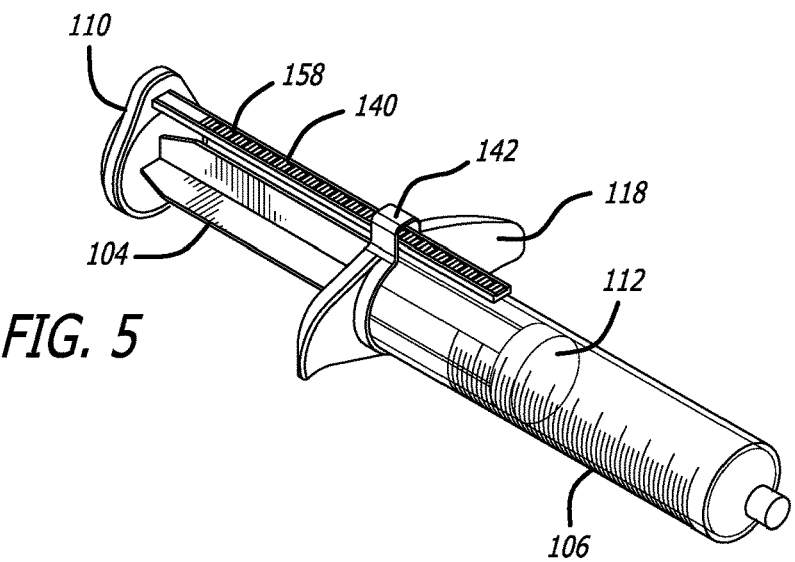
FIG. 5 illustrates another perspective view of a variation of the accessory illustrated in FIG. 4 attached to a standard syringe.
Figure 6:
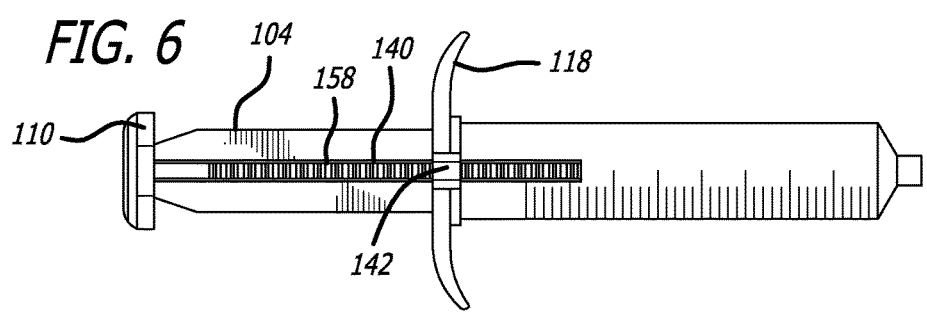
FIG. 6 illustrates a side view of the accessory illustrated in FIG. 5.
Figure 7:
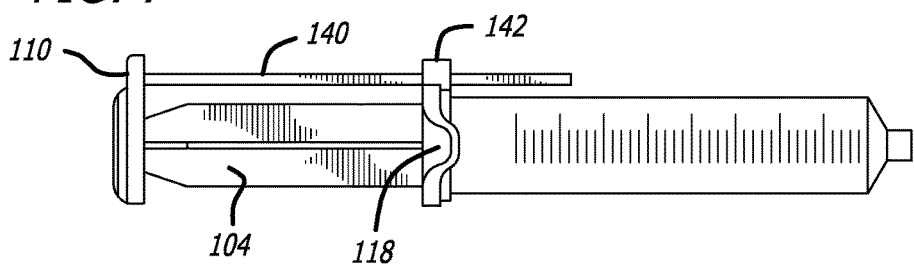
FIG. 7 illustrates a second side view of the accessory illustrated in FIG. 5.
Figure 8:
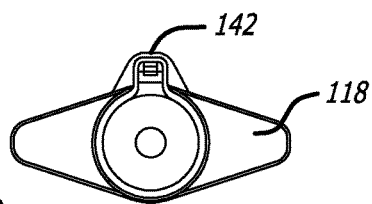
FIG. 8 illustrates a bottom view of the accessory illustrated in FIG. 5.
Figure 9:
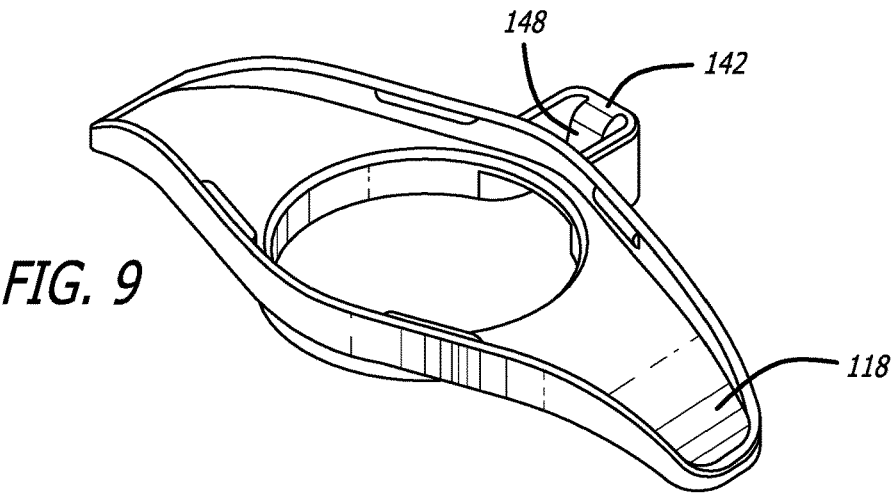
FIG. 9 illustrates a perspective view of the flange portion including a track guide of the accessory illustrated in FIGS. 4 and 5.
Figure 10:
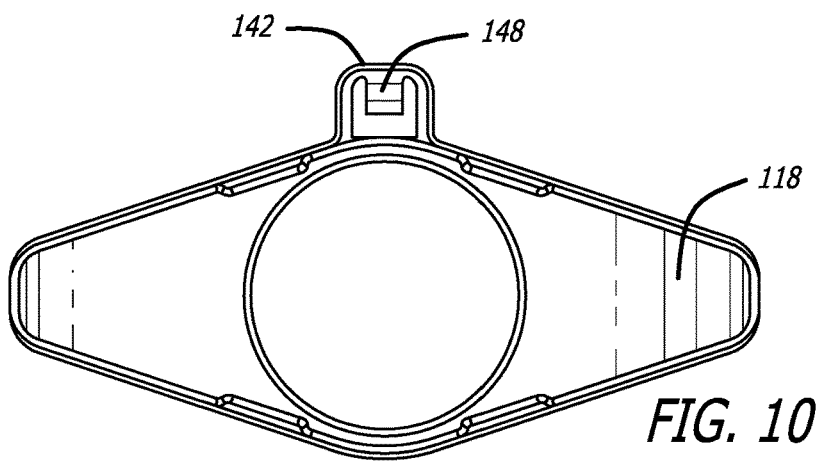
FIG. 10 illustrates a top view of the flange portion illustrated in FIG. 9.
Figure 11:
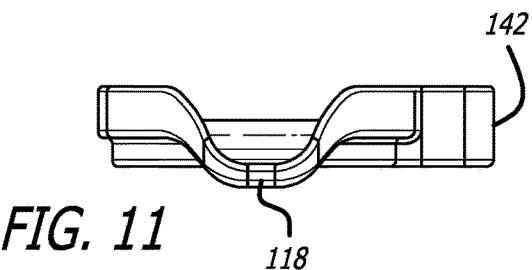
FIG. 11 illustrates a side view of the flange portion illustrated in FIG. 9.
Figure 12:
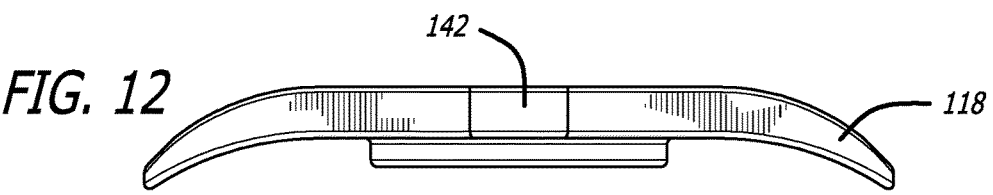
FIG. 12 illustrates a second side view of the flange portion illustrated in FIG. 9.
Figure 13:
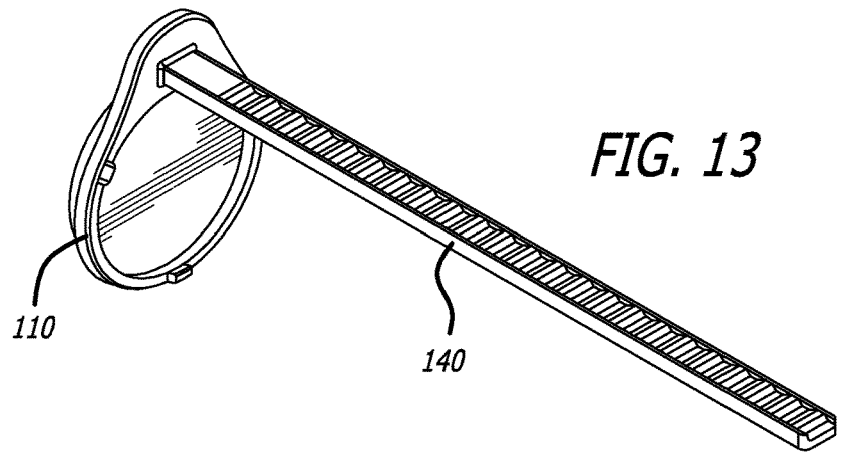
FIG. 13 illustrates a perspective view of a track and plunger cover of the accessory illustrated in FIG. 5.
Figure 14:
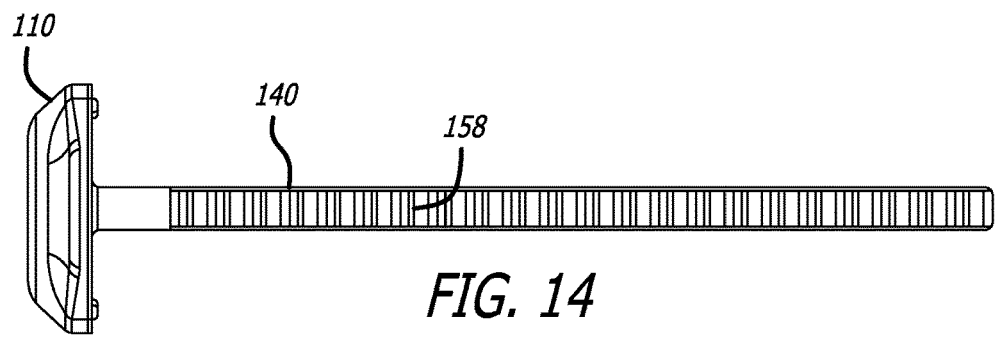
FIG. 14 illustrates a side view of the track and plunger cover illustrated in FIG. 13.
Figure 15:
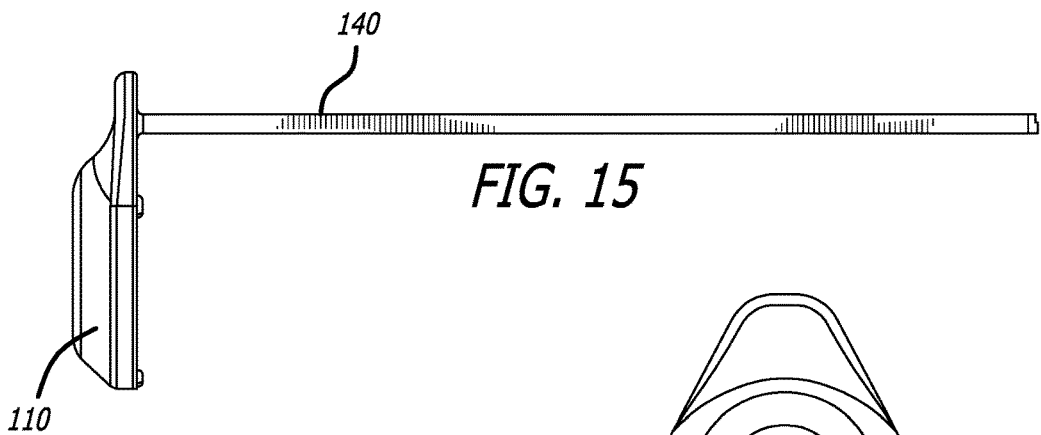
FIG. 15 illustrates a second side view of the track and plunger cover illustrated in FIG. 13.
Figure 16:
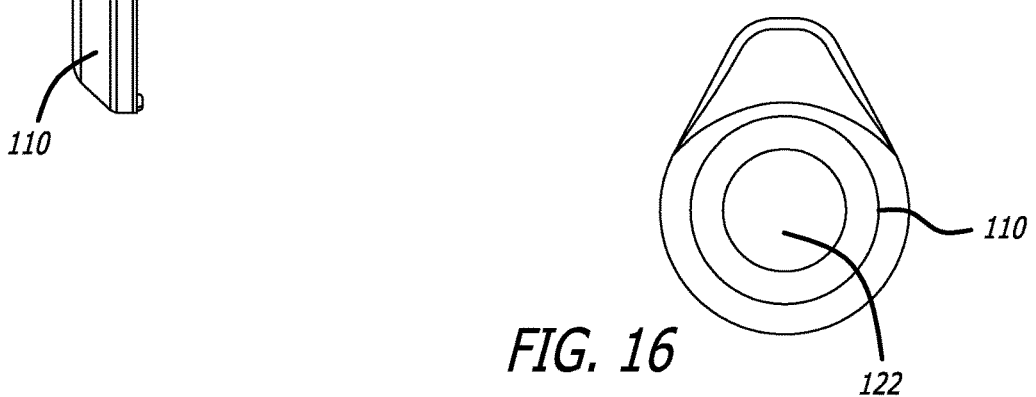
FIG. 16 illustrates a top view of the track and plunger cover illustrated in FIG. 13.
Figure 17:
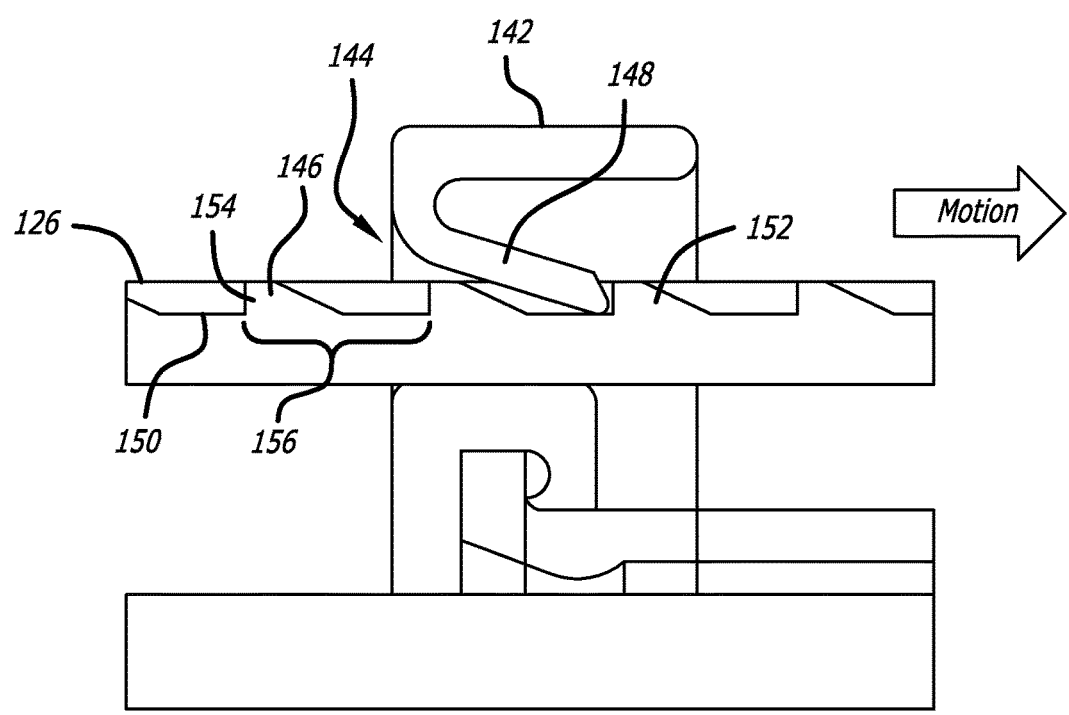
FIG. 17 illustrates a sectional view of a track engaged with a track guide.

In some embodiments, as ratcheting teeth 146 are progressed, the level arm 148 drops into each valley 150 and creates an audible "snap" or other sound and/or provides a tactile feedback. In one embodiment as illustrated in FIG. 5, each tooth of ratcheting teeth 146 can have two or more ridges 158 on long front surface 152. These ridges 158 can provide audible and tactile feedback as lever arm 148 progresses across the ridges and then a larger feedback when lever arm snaps into a valley 150.

Figure 18:
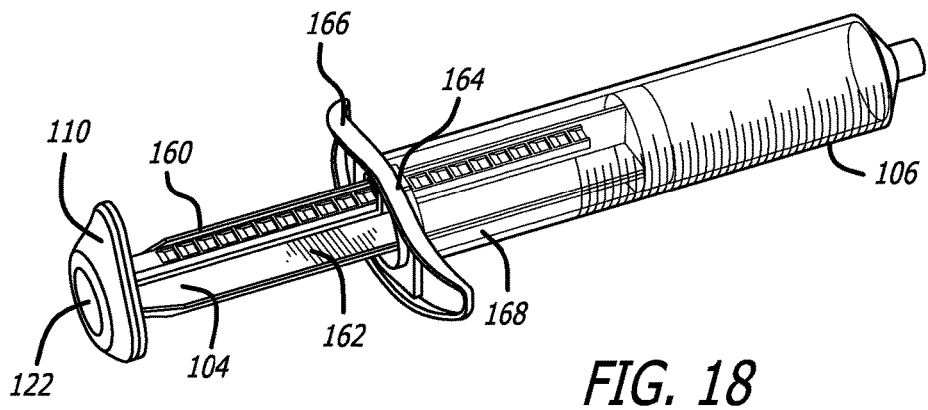
FIG. 18 illustrates an accessory of FIG. 4 or 5 integrated into a syringe.

In another embodiment, as illustrated in FIG. 18, an accessory as described herein can be built into a syringe. For example, track 160 can be built into a plunger stem 162 and a track guide 164 and lever arm can be built into flange 166 of a syringe. As plunger 104 is progressed, track 160 along with plunger stem 162 progresses into barrel 168.

In this built-in embodiment, the plunger including a track can be manufactured as a single unit or can be produced separately and assembled, such as by welding or gluing the track to the plunger stem. Likewise, the syringe barrel and flange including a track guide can be manufactured as a single unit or can be produced separately and assembled, such as by welding or gluing the flange including a track guide to the barrel flange.

The accessories described herein can be operated as follows. First, a user can match an accessory for an appropriately sized syringe. Also, a user can match an appropriately sized syringe for a particular accessory.

Then, flange portion 118 can be snapped or otherwise engaged with syringe flange 120. A track guide 116 can then be attached to the flange portion if not already provided as a single piece with flange portion 118.

Then, holding the syringe upwards, insert the track into the track guide and click the track through the track guide until plunger cover 110 rests against the plunger head. The plunger cover 110 can then optionally be attached to the plunger head. In some embodiments, at this point, the device is ready to use.

In one exemplary embodiment, an injection device is provided comprising a syringe including a distal end connectable to a cannula, a barrel in the syringe body suitable to contain an injectable substance, and a plunger having a proximal actuating end or plunger head and a distal head or piston movable within the barrel for forcing the injectable substance toward the syringe distal end. In some embodiments, this injection device is a standard syringe. An accessory can be attached to this injection device, the accessory including a ratchet assembly including a collar connectable to the syringe barrel or flange, a toothed portion slidably extending through the collar and a cap or plunger cover engageable with the proximal actuating end of the plunger, for facilitating aliquot or dosing of the injectable substance. In one embodiment, the accessory can include a ratchet assembly as shown and described herein. The assembly can be sized and configured for functional engagement with a standard, conventional, for example, a 10 cc, syringe. In other embodiments, the syringe can be a 1 cc, 2 cc, 3 cc, 4 cc, 5 cc, 6 cc, 7 cc, 8 cc, 9 cc, 10 cc, 15 cc, 20 cc, 50 cc, 100 cc, 500 cc, between 1 cc and 2 cc, between 1 cc and 20 cc, or between 5 cc and 20 cc.

Also described herein are accessories configured to prevent over-dosing for a prescribed aliquot amount. These accessories can provide discrete amounts of plunger travel that can translate into discrete aliquot or dosed injection amounts. These accessories in some embodiments require that a user simply attach the accessory to a standard syringe.

These accessories can provide feedback in the form of a tactile or sensory cue, while the syringe by itself provides standard visible volumetric marks.

The accessories can provide feedback for a completed dose as well as can prevent accidental multiple dosing. For example, such an accessory may be useful when a material or substance being extruded from the syringe is non-homogeneous and has flow characteristics that vary throughout an injection. In this circumstance of a non-homogeneous substance, the user may exert a significant amount of force to extrude a highly viscous portion of the substance, but that may be followed by a low viscosity portion of the substance. When the lower viscosity portion of the substance is reached, the significant amount of force required to extrude the highly viscous portion may become uncontrollable and result in overdosing. Therefore, it is possible that too much substance may be delivered. The accessory described herein prevents the overdose or "overshoot" described above.

Figure 19:
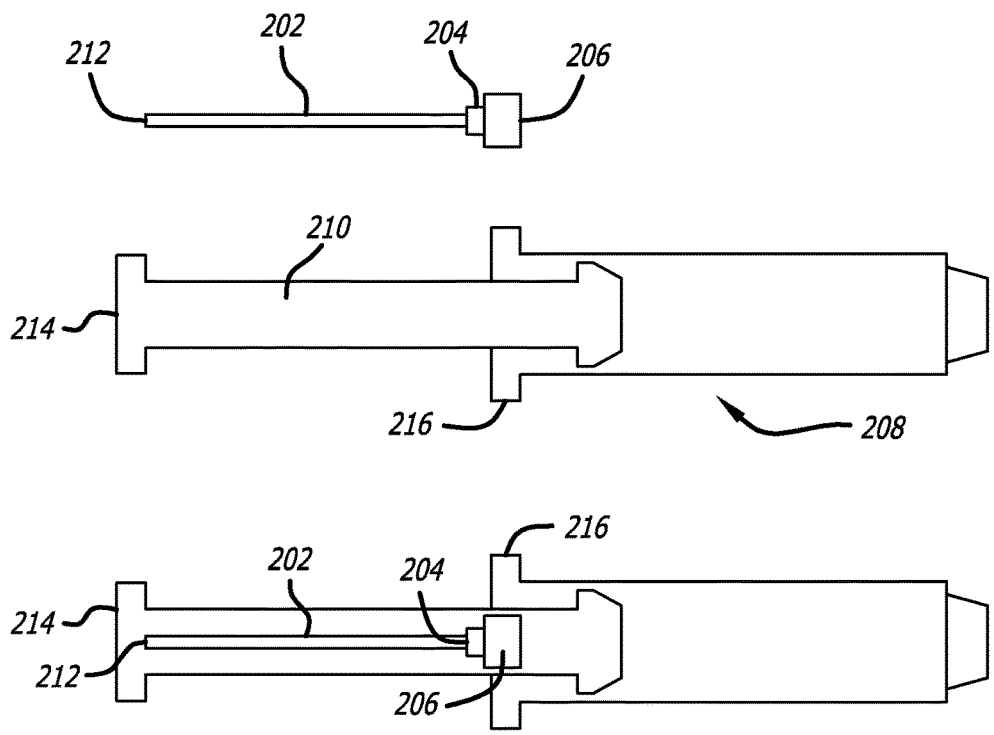
FIG. 19 illustrates another accessory as described herein.
Figure 20:
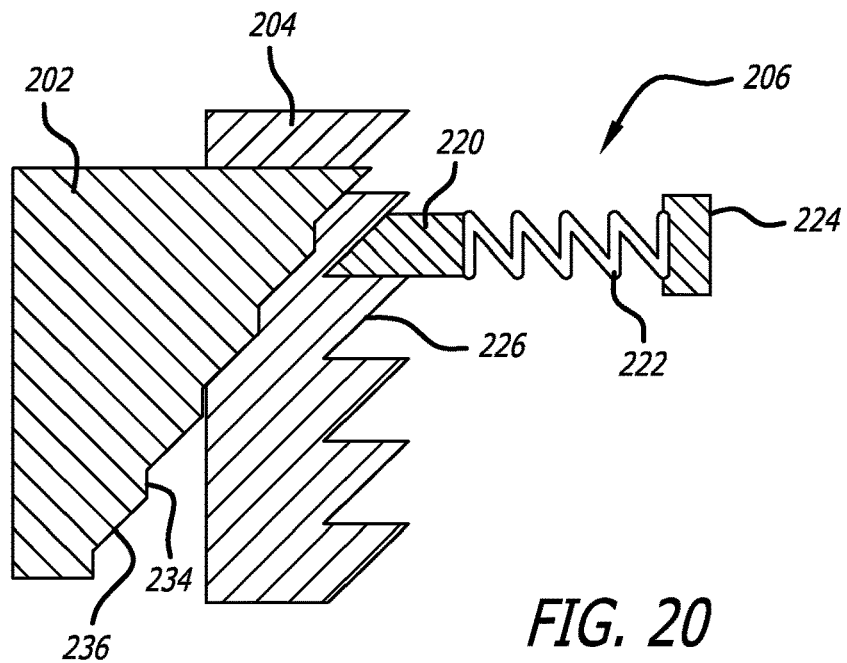
FIG. 20 is a two-dimensional representation of the components used in the accessory illustrated in FIG. 19.

An accessory as illustrated in FIG. 19 can include a separate mechanism that can be attached to a variety of standard size syringes. In other embodiments, the accessory can be built into a syringe.

Accessory 200 can include three main components, those being a shaft 202, a fixed ratchet 204, and a rotating traveler 206. The geometry of the features in shaft 202 can ultimately determine what dose increment is allowed to be extruded from the syringe 208 when a force is applied to a syringe plunger 210. Shaft 202 geometry controls the displacement which in turn controls the volume delivered per dose.

In one embodiment, distal portion 212 of shaft 202 is connected to plunger 210, plunger head 214, plunger cover 110, or a combination thereof. These components move in unison together once assembled.

Fixed ratchet 204 can be rigidly attached to the syringe 208, for example, at syringe flange 216 area of syringe 208. Rotating traveler 206 can be assembled onto fixed ratchet 204 and shaft 202, and can have a limited rotational and linear travel within accessory 200.

FIGS. 20-23 illustrate a mechanism 218 that is configured to be used in accessory 200. Two-dimensional illustrations of mechanism 218 are illustrated to simplify comprehension. In the 2D representation, the horizontal axis corresponds to the axial direction and the vertical axis corresponds to axial rotation in the 3D renditions. Also, rotating traveler 206 interacts with both shaft 202 and fixed ratchet 204. However, in some embodiments, shaft 202 and fixed ratchet 204 do not interface with each other directly.

Figure 21:
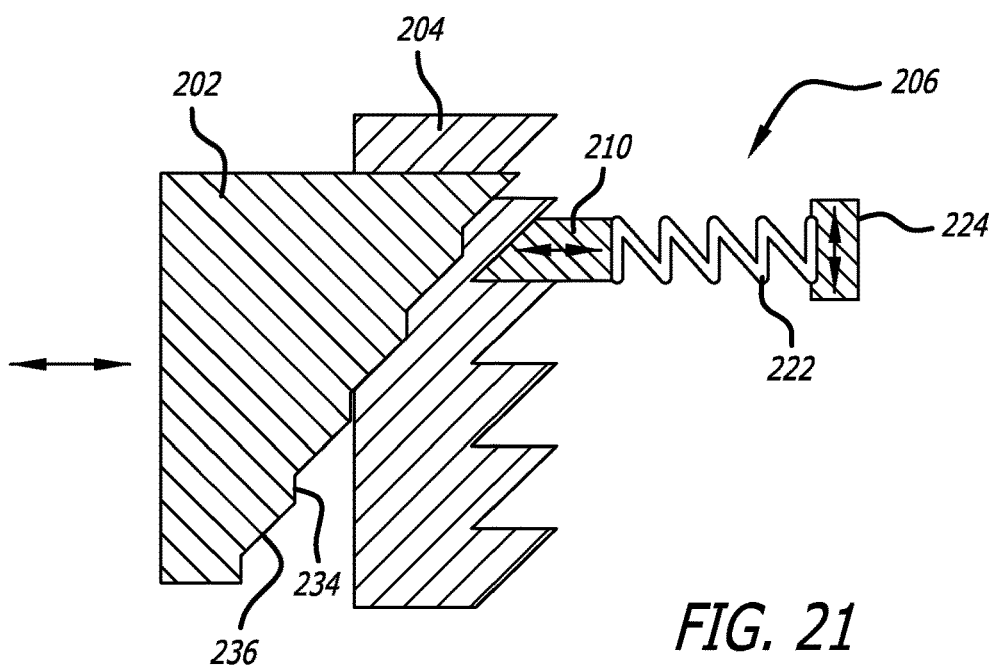
FIG. 21 is another two-dimensional representation of the components used in the accessory illustrated in FIG. 19 showing degrees of freedom.
Figures 22A, 22B, 22C, 22D:
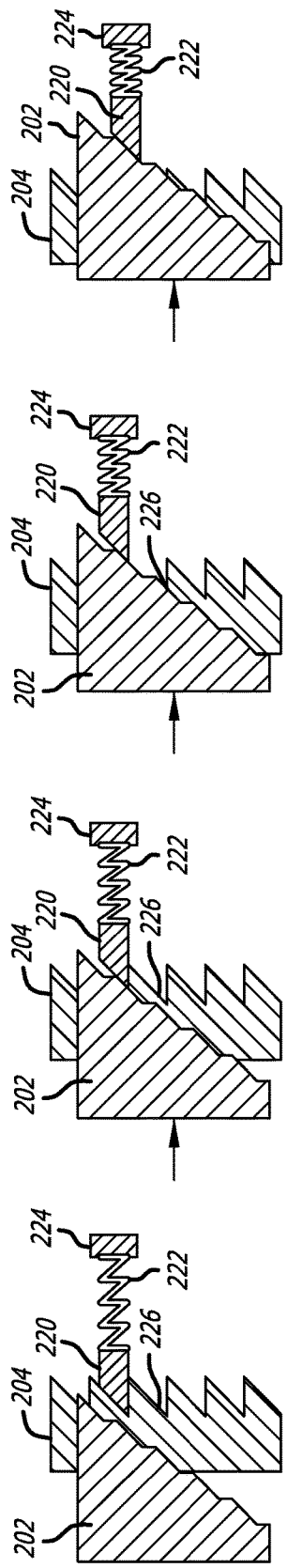
FIGS. 22A-23B are two-dimensional representations of the steps for using the accessory illustrated in FIG. 19. Each of FIGS. 22A-23B can represent a step or a portion of a step in using the accessory illustrated in FIG. 19.
Figure 22E:
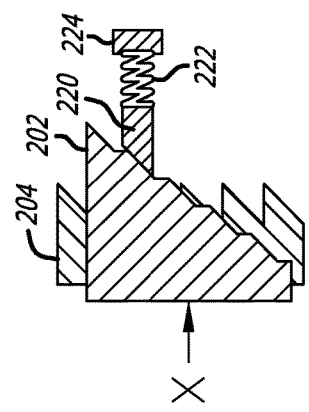
Figure 23A:
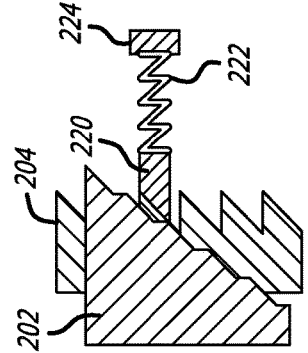
Figure 23B:
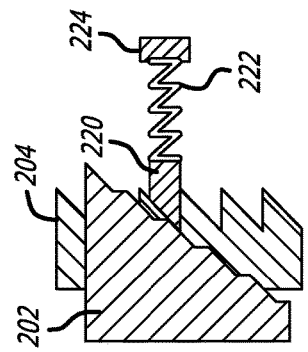

The arrows illustrated in FIG. 21 indicate degrees of freedom for each component. Fixed ratchet 204 is rigidly fixed relative to the syringe housing and therefore may not have any degrees of freedom. Shaft 202 can move horizontal relative to fixed ratchet 204 but cannot rotate (in the 2D renditions, this corresponds to not moving vertically). An interface portion 220 of rotating traveler 206 can move horizontally. This horizontal motion is driven by compression spring 222. Rotating traveler 206 as a whole including base portion 224 can be allowed to rotate freely (in 2D renditions, this corresponds to vertical movement).

FIGS. 22A-23B illustrate how shaft 202 advances one step 226 on the fixed ratchet 204 at a time. Note that when pressure is released from shaft 202 (and is allowed to move to the left), the accessory resets to a next step and shaft 202 is allowed to continue advancing.

Accessory 200 can be configured to function as follows. After the accessory is attached to a standard syringe, accessory is in a nominal state. In the nominal state, a spring force exists in spring 222 thereby pressing rotating traveler 220 into a step 226 of fixed ratchet 204. Then, when plunger 210 is depressed, shaft 202 moves right thereby moving rotating traveler 206 and compressing spring 222. Shaft 202 moves far enough and compresses rotating traveler 206 via spring 222 so that rotating traveler 206 moves down (rotates) as spring 222 causes rotating traveler 206 to slide along shaft 202. When spring 222 reaches full compression, or compressed solid height, the user feels a hard stop indicating that a dose has been delivered.

Then, a user releases plunger 210 and the compression force of spring 222 is released and rotating traveler 206 shifts back against shaft 202. As shaft 202 is forced back through compression force being released by spring 222, rotating traveler 206 again interfaces with fixed ratchet 204 causing rotating traveler 206 to move down (rotate) and slip into next step 226 on fixed ratchet 204. Notice that shaft 202 will reengage at next step feature, allowing shaft 202 to incrementally move to the right.

At this point, a subsequent dose can be delivered.

Figure 24:
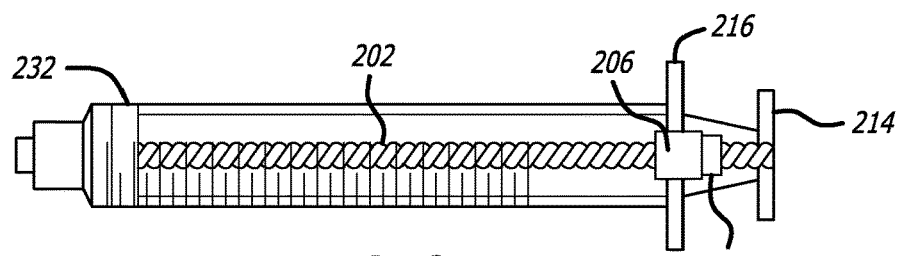
FIG. 24 illustrates the accessory illustrated in FIG. 19 integrated with a syringe.

FIG. 24 illustrates how accessory 200 can be oriented with a syringe. Shaft 202 can have a generally spiral shape or configuration and can serve as a plunger stem. Shaft 202 can be connected to piston 232 and plunger head 214 thereby creating a plunger assembly. In other embodiments, shaft 202 can simply be associated with a plunger similar to that of tracks in FIG. 4. In other embodiments, shaft 202 can simply abut against piston 232 and be used to apply a force thereto once in contact.

Rotating traveler 206 and fixed ratchet 204 can be associated with syringe flange 216. In some embodiments, rotating traveler 206 and fixed ratchet 204 can be built into a syringe flange. In other embodiments, rotating traveler 206 and fixed ratchet 204 can be attachable to a syringe flange and can even be reusable.

Figure 25:
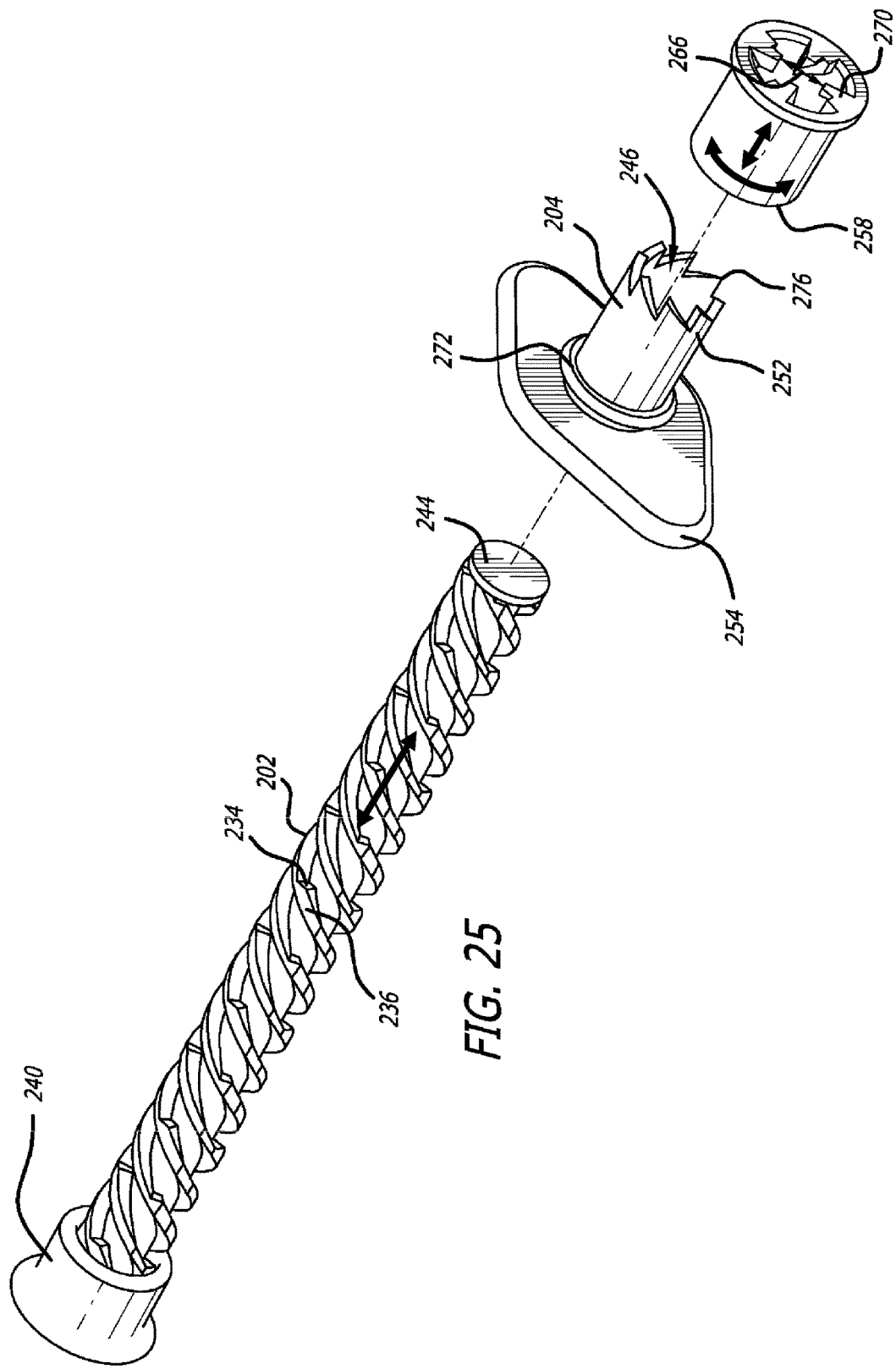
FIG. 25 illustrates a perspective exploded view of example components used with the accessory illustrated in FIG. 19.

Example components used to assemble accessory 200 are illustrated in FIGS. 25-27. Therein, shaft 202 can have a spiral configuration axially along the shaft. The shaft is intended to be driven to the right. In some embodiments, the spiral configuration runs substantially the entire length of shaft 202. The spiral configuration can include stops 234 along spiral 236. These stops can be seen on the shaft in FIG. 25. Each spiral can include multiple stops and a predetermined distance can exist between each stop. This predetermined distance can translate into distance 228 which is a distance traveled by the plunger.

On distal end 238 of shaft 202 can exist a plunger accessory 240. Plunger accessory 240 can interface with a plunger head or can itself be a plunger head for a syringe. Further, plunger accessory 240 can be configured to freely rotate around shaft 202. Or, in other words, as shaft 202 rotates freely, plunger accessory 240 can remain fixed. This free rotation can allow force to be applied to a plunger head while allowing shaft 202 to rotate about spiral 236. In other embodiments, plunger accessory 240 can be fixed to shaft 202.

Proximal end 242 of shaft 202 can include surface 244. Surface 244 can interface with a plunger piston. A piston can attach to surface 244, and like plunger accessory 240, shaft 202 can rotate freely within a plunger piston. In other embodiments, plunger accessory 240 can be fixed to shaft 202.

Fixed ratchet 204 can have a hole 246 that has an inner diameter 248 that is larger than the outer diameter 250 of shaft 202. This larger diameter allows shaft 202 to be guided through hole 246 in fixed ratchet 204. Fixed ratchet 204 further includes multiple steps 226 at distal end 252. Fixed ratchet 204 can include one, two, three, four, five, six, seven, eight, nine, ten, or more steps. In one embodiment, fixed ratchet 204 includes eight steps. Fixed ratchet 204 can also include a flange portion 254 at proximal end 256 that can serve as a flange or interface with a syringe flange.

Rotating traveler 206 can have a generally cylindrical shape with an open proximal end 258. The inner diameter 260 of rotating traveler 206 can be larger than the outer diameter 262 of fixed ratchet 204 allowing rotating traveler 206 to fit over fixed ratchet 204. Rotating traveler can further include an annular shaped distal end 264.

Distal end 264 can further include a hole with a diameter 266 that is slightly larger than inner spiral diameter 268 of shaft 202. Diameter 266 can be created by one or more teeth 270 on rotating traveler 206. Rotating traveler 206 can include one, two, three, four, five, six, seven, eight, nine, ten, or more teeth. In one embodiment, rotating traveler includes four teeth. Teeth 270 can be configured to interact with steps 226 on fixed ratchet 204 and spiral 236 and stops 234 on shaft 202.

Fixed ratchet 204 can further include a stop 272 that can stop proximal end 258 of rotating traveler 206 even if teeth 270 happen to skip over a stop 234 on shaft 202. In some embodiments, stop 272 can be a ring or other circumferential protrusion that can interact and stop proximal end 258 of rotating traveler 206.

In order to use the assemblage of FIGS. 25-27, force can be applied to plunger accessory 240 such that shaft 202 is driven axially through hole 246. As shaft is driven axially, teeth 270 travel along spiral 236. As teeth 270 travel along spiral 236, rotating traveler 206 spins as needed. Eventually, teeth 270 will hit a stop 234 and prevent further axial movement of shaft 202. The only way to move teeth 270 past stop 234 is to relieve the force on plunger accessory 240 thereby moving fixed ratchet 204 against teeth 270 thereby spinning rotating traveler enough to move teeth 270 past stop 234. Then, force can again be applied to plunger accessory 240 and the process started again.

Figure 28A:
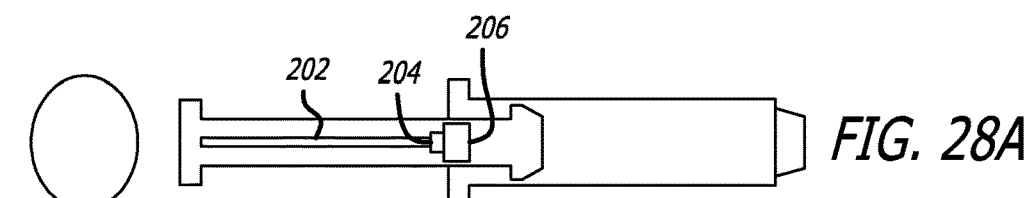
FIGS. 28A-G illustrate exemplary steps for using the accessory illustrated in FIG. 19.
Figure 28B:
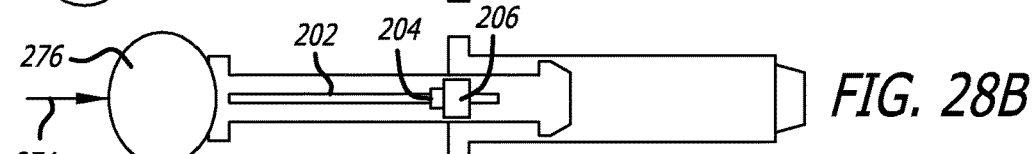

FIGS. 28A-G illustrate one example use scenario for accessory 200. Prior to injection, at the stage of FIG. 28A, accessory 200 is assembled onto syringe 208. Then, as illustrated in FIG. 28B, a user presses or applies force 274 to plunger 210, for example using finger 276, to inject the substance housed in syringe 208.

Figure 28C:
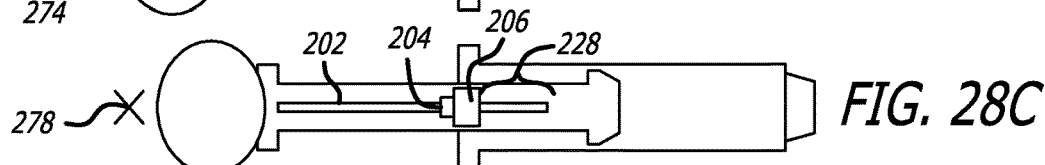

At a distance 228 corresponding to the geometry of shaft 202, a hard stop is encountered and a tactile feedback 278 is felt in finger 276. This is illustrated in FIG. 28C. Continued force or pressure on plunger 210 by the user will not advance the plunger any further.

Figure 28D:
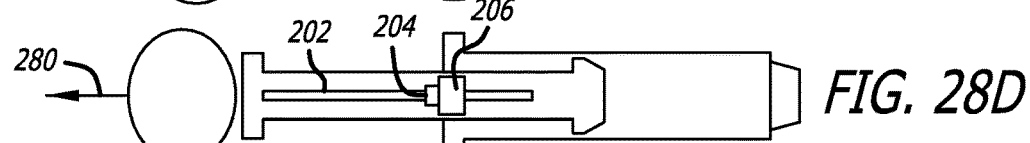
Figure 28E:
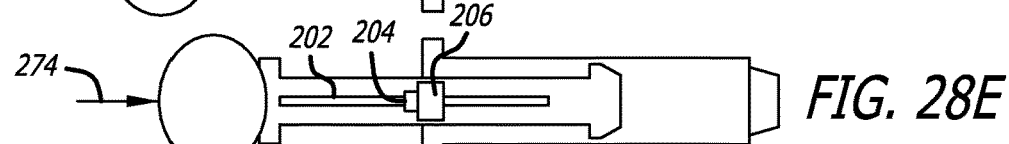

Then, as illustrated in FIG. 28D, the user temporarily releases force 280 or pressure on the plunger and the mechanism in accessory 200 resets, allowing another dose to be delivered. Another dose can be injected by applying force 274 again to plunger 210 (FIG. 28E).

Figure 28F:
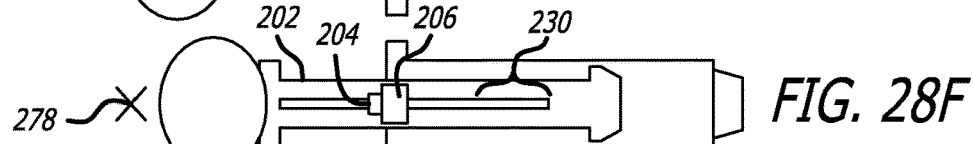
Figure 28G:
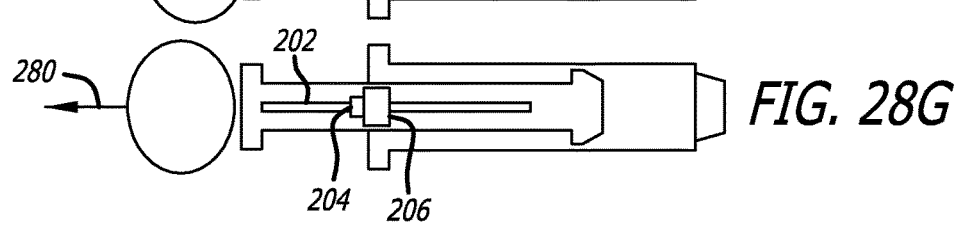

Again, at distance 230 corresponding to the geometry of the shaft, here identical to distance 228, a hard stop is encountered, and continued pressure by the user will not advance plunger 210 any further (FIG. 28F). Then, again, the user temporarily releases force from plunger 210 and the mechanism resets, allowing another dose to be injected (FIG. 28G).

This method can be repeated until the contents of syringe 208 have been depleted or until a sufficient number of doses have been injected.

In some embodiments, accessory 200 can further include a harness to attach accessory 200 to a standard syringe flange. The harness can be configured to be a two piece component that snaps or otherwise locks around the flange of a syringe and stop 272. By locking the two components together, surface 244 can engage the plunger or piston of the standard syringe and any force applied to plunger accessory 240 can be translated to force upon the standard syringe piston.

Figure 4:
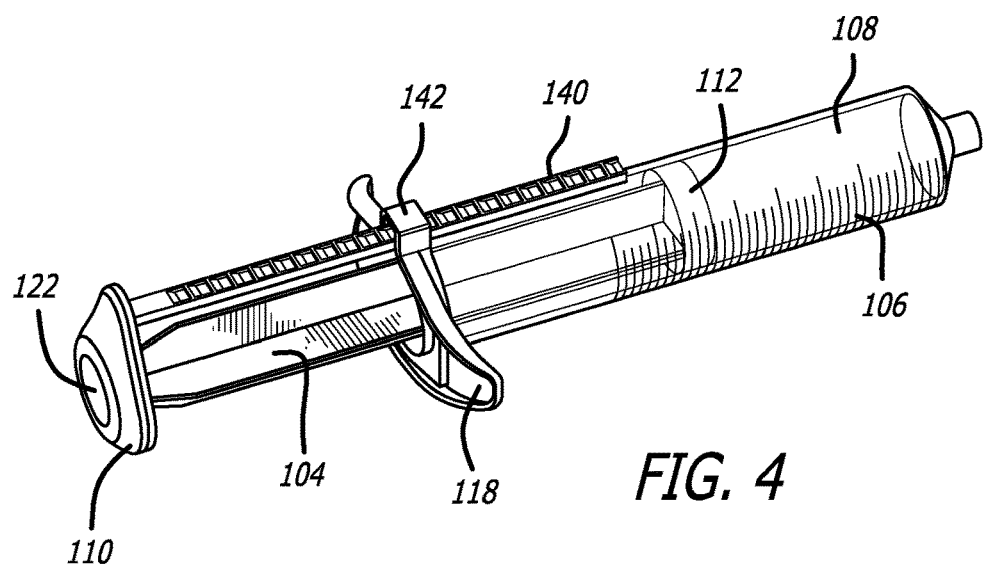
FIG. 4 illustrates a perspective view of another example accessory as described herein attached to a standard syringe.

Additionally, depending on the spacing of the ratcheting teeth or valleys, different accessories described herein can be configured for different aliquot/dosing requirements. Any dosing increment can be configured into an accessory described herein. In some embodiments, for example, dosing increments can be configured to be 0.1 mL, 0.5 mL, 1 mL, 1.5 mL, 2 mL, 2.5 mL, 3 mL, 3.5 mL, 4 mL, 4.5 mL, 5 mL, between about 0.1 mL and about 5 mL, between about 1 mL and about 5 mL, between about 1 mL and about 3 mL, or between about 0.1 mL and about 3 mL. In one embodiment, the accessory illustrated in FIGS. 2-3 is configured to have a dosing increment of 1 mL. In another embodiment, the accessory illustrated in FIGS. 4-5 is configured to have a dosing increment of 3 mL.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An accessory for a syringe comprising:
    a shaft including a spiral and a plurality of intermittent stops disposed along the spiral, wherein a distance between a first one of the intermittent stops and a second one of the intermittent stops is configured to define a dose increment, wherein the shaft has a first translational degree of freedom and does not have any rotational degree of freedom relative to a barrel of the syringe;
    a rotating traveler having a second translational degree of freedom and a rotational degree of freedom relative to the barrel; and
    a fixed ratchet including valleys configured to engage the rotating traveler,
    wherein the shaft is at least partially attached to a plunger of the syringe.

2. The accessory of claim 1, wherein the fixed ratchet is attached to a flange on the syringe.

3. The accessory of claim 1, wherein the shaft is configured to move with the first translational degree of freedom to engage the rotating traveler.

4. The accessory of claim 1, wherein the rotating traveler includes a spring that provides the second translational degree of freedom.

5. The accessory of claim 1, wherein the shaft is configured to move within the barrel to reach a first dose increment upon application of pressure by a user, and wherein the shaft is configured to reset for a subsequent dose increment upon removal of the pressure.

6. The accessory of claim 1, wherein the rotating traveler is configured to spin around the spiral.

7. The accessory of claim 1, wherein the valleys of the fixed ratchet do not interact with the shaft.

8. The accessory of claim 1, wherein the fixed ratchet does not have any degree of freedom relative to the barrel.

9. The accessory of claim 1,
    wherein, when the plunger is depressed in a distal direction, the shaft is configured to move with the first translational degree of freedom to compress a spring, and
    wherein, when the plunger is released, the spring is configured to urge the shaft in a proximal direction.

10. The accessory of claim 9, wherein, when the plunger is released by a user, the rotating traveler is configured to rotate toward a next step of the fixed ratchet.

11. An accessory for a syringe comprising:
    a shaft defining a longitudinal axis and having a plurality of stops, each of the stops being associated with a predetermined dose increment, the shaft being rotatably fixed about the longitudinal axis and translatable along the longitudinal axis relative to a barrel of the syringe to eject the predetermined dose increment;
    a ratchet component being translatably fixed along and rotatably fixed about the longitudinal axis, the ratchet component including a series of peaks and valleys extending circumferentially about the longitudinal axis; and
    a traveler component having a base portion and a spring-loaded interface portion coupled to the base portion, the base portion being translatably fixed along and rotatable about the longitudinal axis, the spring-loaded interface portion being engageable with the ratchet component in a first rotational position of the traveler component to restrict rotation of the traveler component about the longitudinal axis, the spring-loaded interface portion further being longitudinally compressible along the longitudinal axis in response to contact with and translation of the shaft during ejection of the predetermined dose increment, the spring-loaded interface portion being configured to urge rotation of the traveler component toward a second rotational position about the longitudinal axis during compression of the spring-loaded interface portion, the spring-loaded interface portion being configured to be fully compressed against a given stop of the shaft for limiting longitudinal translation of the shaft to permit ejection of only the predetermined dose increment, the spring-loaded interface portion being configured to rebound toward and engage with the ratchet component in the second rotational position to restrict further rotation of the traveler component relative to the ratchet component.

12. The accessory of claim 11, wherein the shaft is configured to translate distally to engage with and compress the spring-loaded interface portion, and wherein a spring force of the spring-loaded interface portion is configured to cause the shaft to translate proximally.

13. The accessory of claim 11, wherein the ratchet component comprises a plurality of teeth.

14. The accessory of claim 11, wherein the shaft comprises a spiral contacting edge having a plurality of spiral portions, each of the spiral portions being positioned between a given pair of stops of the plurality of stops along the spiral contacting edge.

15. A metered dose syringe comprising:
a syringe barrel defining a longitudinal axis;
a plunger shaft longitudinally movable within and rotatably fixed relative to the syringe barrel, the plunger shaft having a distal edge and a plurality of stops disposed along the distal edge for providing a predetermined dose increment; and
a dosage feedback mechanism including a ratchet component and a traveler component, the ratchet component being translatably and rotatably fixed relative to the syringe barrel, the ratchet component including a series of peaks and valleys extending circumferentially about the longitudinal axis, the traveler component having a base portion and a spring-loaded interface portion coupled to the base portion, the base portion being translatably fixed relative to the syringe barrel and rotatable about the longitudinal axis,
wherein the spring-loaded interface portion is engageable with the ratchet component to restrict rotation of the traveler component, the plunger shaft being depressible to (i) contact the distal edge thereof against the spring-loaded interface portion, (ii) cause rotation of the traveler component about the longitudinal axis, and (iii) fully compress the spring-loaded interface portion against a given stop of the plurality of stops of the distal edge for limiting longitudinal translation of the plunger shaft to permit ejection of only the predetermined dose increment.

16. The metered dose syringe of claim 15, wherein the spring-loaded interface portion is configured to rebound toward and engage with the ratchet component to restrict further rotation of the traveler component relative to the ratchet component.

17. The metered dose syringe of claim 15, wherein the distal edge comprises a plurality of spiral portions, each of the spiral portions being positioned between a given pair of stops of the plurality of stops along the distal edge.

18. The metered dose syringe of claim 15, wherein the ratchet component comprises a plurality of teeth.

* * * * *